(12) United States Patent
Oezyilmaz et al.

(10) Patent No.: US 10,316,290 B2
(45) Date of Patent: Jun. 11, 2019

(54) METHOD FOR CONTROLLING DIFFERENTIATION OF STEM CELLS USING GRAPHENE SUBSTRATES

(75) Inventors: Barbaros Oezyilmaz, Singapore (SG); Giorgia Pastorin, Singapore (SG); Henrik Andersen, Singapore (SG)

(73) Assignee: National University of Singapore, Singapore (SG)

( * ) Notice: Subject to any disclaimer, the term of this patent is extended or adjusted under 35 U.S.C. 154(b) by 55 days.

(21) Appl. No.: 13/805,328

(22) PCT Filed: Jul. 8, 2011

(86) PCT No.: PCT/SG2011/000247
§ 371 (c)(1),
(2), (4) Date: Dec. 18, 2012

(87) PCT Pub. No.: WO2012/005699
PCT Pub. Date: Jan. 12, 2012

(65) Prior Publication Data
US 2013/0095083 A1    Apr. 18, 2013

Related U.S. Application Data

(60) Provisional application No. 61/362,506, filed on Jul. 8, 2010.

(51) Int. Cl.
*C12N 5/0775* (2010.01)
*A61K 35/32* (2015.01)
(Continued)

(52) U.S. Cl.
CPC .............. *C12N 5/0663* (2013.01); *A61K 9/00* (2013.01); *A61K 35/32* (2013.01); *A61L 27/3834* (2013.01); *C12N 2533/10* (2013.01)

(58) Field of Classification Search
CPC ......... A61F 2210/0004; A61F 2/30767; C12N 5/00; C12N 5/0675; C12N 5/0062;
(Continued)

(56) References Cited

U.S. PATENT DOCUMENTS

2008/0038814 A1    2/2008  Huie
2009/0041825 A1    2/2009  Kotov et al.
(Continued)

FOREIGN PATENT DOCUMENTS

WO    WO 2010/065551 A2    6/2010
WO    WO 2010/117389 A1    10/2010

OTHER PUBLICATIONS

Li-2 et al., Nature, 3:101-105, 2008.*
(Continued)

*Primary Examiner* — Allison M Fox
*Assistant Examiner* — Qing Xu
(74) *Attorney, Agent, or Firm* — Hamilton, Brook, Smith & Reynolds, P.C.

(57) ABSTRACT

The invention relates to methods for directing differentiation of stem cells comprising graphene. In additional embodiments, the invention relates to methods for repairing and improving bone tissue functions comprising accelerating differentiation in stem cell growth by exposing stem cells to graphene and transplanting the graphene with the exposed stem cells in the tissue at the site of repair.

14 Claims, 5 Drawing Sheets

(51) Int. Cl.
*A61K 9/00* (2006.01)
*A61L 27/38* (2006.01)

(58) Field of Classification Search
CPC . A61K 9/00; A61K 33/44; B82Y 5/00; C01B 31/04; C01B 31/0206
See application file for complete search history.

(56) References Cited

U.S. PATENT DOCUMENTS

2009/0148417 A1 6/2009 Kim et al.
2010/0104652 A1 4/2010 Biris et al.
2012/0076830 A1* 3/2012 Sitharaman et al. ......... 424/400

OTHER PUBLICATIONS

Baik et al. Small, 7(6):741-745, published in Feb. 2011. (Year: 2011).*
Lee, W., et al., "Carbon Nanotubes as Substrates/Scaffolds for Neural Cell Growth," *Progress in Brain Research*, 180: 111-125 (2009).
Mooney, E., et al., "Carbon Nanotubes and Mesenchymal Stem Cells: Biocompatibility, Proliferation and Differentiation," *Nano Letters*, 8(8): 2137-2143 (2008).
Tay, C.Y., et al., "Cellular Behavior of Human Mesenchymal Stem Cells Cultured on Single-Walled Carbon Nanotube Film," *Carbon*, 48(4): 1095-1104 (2010).
Chao, T.I., et al., "Carbon Nanotubes Promote Neuron Differentiation from Human Embryonic Stem Cells," *Biomechanical and Biophysical Research Communication*, 384(4): 426-430 (2009).
Park, S.Y., et al., "Carbon Nanotube Monolayer Patterns for Directed Growth of Mesenchymal Stem Cells," *Advanced Materials*, 19(18): 2530-2534 (2007).
McCullen, S.D., et al., "Characterization of Electrospun Nanocomposite Scaffolds and Biocompatibility With Adipose-Derived Human Mesenchymal Stem Cells," *International Journal of Nanomedicine*, 2(2): 253-263 (2007).
Kalbacova, M., et al., "The Study of the Interaction of Human Mesenchymal Stem Cells and Monocytes/ Macrophages With Single-Walled Carbon Nanotube Films," *Physica Status Solidi* (b), 243(13): 3514-3518 (2006).
Holy, J., et al., "Differentiation of Pluripotent Stem Cells on Multiwalled Carbon Nanotubes," *31st Annual International Conference of the IEEE, Minneapolis, MN* Sep. 2-6, 2009, 6002-6025.
Penalver, J.L., et al., "Activated Carbon Cloth as Support for Mesenchymal Stem Cell Growth and Differentiation to Osteocytes," *Carbon*, 47(15): 3574-3577 (2009).
Sridharan, K., et al., "Adapting Collagert/CNT Matrix in Directing hESC Differentiation," *Biochemical and Biophysical Research Communication*, 381(4): 508-512 (2009).
Bakture, R., et al., "Carbon Nanotube-Collagen Scaffolds for Mesenchymal Stem Cells' Differentiation: Changes in Alkaline Phosphatase Expression, Meneralizaton, and Energy Content," *Nanotech Conference and Expo, 2010*.
Ferreira, L., et al., "New Opportunities: The Use of Nanotechnologies to Manipulate and Track Stem Cells," *Cell Stem Cell*, 3(2): 136-146 (2008).
Malarkey, E.B. and V. Parpura, "Applications of Carbon Nanotubes in Neurobiology," *Neurodegenerative Disease*, 4(4): 292-299 (2007).
Kalbacova, M., et al., "Graphene Substrates Promote Adherence of Human Osteoblasts and Mesenchymal Stromal Cells," *Carbon*, 48, 4323-4329 (2010).
Notification Concerning Transmittal of International Preliminary Report on Patentability and Written Opinion, PCT/SG2011/000247, "Method for Controlling and Accelerating Differentiation of Stem Cells Using Graphene Substrates" dated Jan. 17, 2013.

International Search Report, PCT/SG2011/000247, "Method for Controlling and Accelerating Differentiation of Stem Cells Using Graphene Substrates" dated Aug. 22, 2011.
Engler, A. J., et al., "Matrix Elasticity Directs Stem Cell Lineage Specification", Cell, 126: 677-689 (Aug. 25, 2006).
Li, X., et al., "Large-Area Synthesis of High-Quality and Uniform Graphene Films on Copper Foils", *Science*, 324: 1312-1314 (Jun. 5, 2009).
Oh, S. et al., "Stem Cell Fate Dictated Solely by Altered Nanotube Dimension", *PNAS USA*, 106 2130-2135 (Feb. 17, 2009).
Written Opinion of the International Searching Authority, PCT/SG2011/000247, "Method for Controlling and Accelerating Differentiation of Stem Cells Using Graphene Substrates", dated Aug. 22, 2011.
Nayak, T.R., et al., "Graphene for Controlled and Accelerated Osteogenic Differentiation of Human Mesenchymal Stem Cells", *ACS Nano*, vol. 5, pp. 4670-4678 (Apr. 29, 2011).
Nayak, T.R., et al., "Thin Films of Functionalized Multiwalled Carbon Nanotubes as Suitable Scaffold Materials for Stem Cells and Proliferation and Bone Formation", *ACS Nano*, 4(12): 7717-7725 (2010).
Czarnecki, J.S., et al., "Hybrid Carbo-Based Scaffolds for Applications in Soft Tissue Reconstruction", *Tissue Engineering: Part A*, 18(9)(10): 946-956 (2012).
Dalby, M.J., et al., "The control of human mesenchymal cell differentiation using nanoscale symmetry and disorder", *Nature Materials*, 6: 997-1003 (Dec. 2007).
Balmayor, E. R., et al., "Starch-poly-ε-caprolactone Microparticles Reduce the Needed Amount of BMP-2", *Clin Orthop Relat Res*, 467: 3138-3148 (2009).
Kim, H.M., et al., "Composition and structure of apatite formed on organic polymer in simulated body fluid with a high content of carbonate ion", *Journal of Materials Science: Materials In Medicine*, II: 421-426 (2000).
Kim, S. J., et al., "Surface modification of polydimethylsiloxane (PDMS) induced proliferation and neural-like cells differentiation of umbilical cord blood-derived mesenchymal stem cells", *J. Matter Sci: Mater Med*, 19: 2953-2962 (2008).
Bae, S., et al., "Roll-To-Roll Production of 30-Inch Graphene Films for Transparent Electrodes," *Nat. Nano*, 5: 574 (2010).
Chen, Z., et al., "Three-Dimensional Flexible and Conductive Interconnected Graphene Networks Grown by Chemical Vapour Deposition," *Nature Materials*, 10: 424-428 (Jun. 2011).
Czarnecki, J.S., et al., "A Novel Approach to Control Growth, Orientation, and Shape of Human Osteoblasts," *Tissue Engineering: Part A*., 14: 255-266 (Nov. 2008).
Dragoo, J.L., et al., "Bone Induction by BMP-2 Transduced Stem Cells Derived From Human Fat" *J. Orthop. Res*, 21(4): 622-629 (2003).
Ercan, B., et al., "Increased Stem Cell Adhesion on Carbon Nanotubes Grown from Anodized Titanium," *Materials Research Society*, 951 0951-E06-28, http://dx.doi.org/10.1557/PROC-0951-E06-28 (2007).
Jaiswal, N., et al., "Osteogenic Differentiation of Purified, Culture-Expanded Human Mesenchymal Stem Cells In Vitro," *J. Cell Biochem.* 64: 295-312 (1997).
Kawai, T., et al., "Coating of an Apatite a Biomimetic Process," *Biomat.* 25, 4529 Layer on Polyamide Films Containing Sulfonic Groups by (2004).
Kim, H.M., et al., "Composition and Structure of the Apatite Formed on PET Substrates in SBF Modified with Various Tonic Activity Products," *Journal of Biomedical Materials Research*, 46(2):228-235 (1999).
Reilly, G.C., et al., "Intrinsic Extracellular Matrix Properties Regulate Stem Cell Differentiation," *J. Biomech.* 43, 55-62 (2010).
Tu, X., et al., "Single-Walled Carbon Nanotube Scaffolds Promote Stem Cell Differentiation into Bone Forming Cells," *Materials Research Society*, 1018, 1018-EE04-09, http://dx.doi.org/10.1557/PROC-1018-EE04-09 (2007).

* cited by examiner

METHOD FOR CONTROLLING DIFFERENTIATION OF STEM CELLS USING GRAPHENE SUBSTRATES

RELATED APPLICATION

This application is the U.S. National Stage of International Application No. PCT/SG2011/000247, filed Jul. 8, 2011, which designates the U.S., published in English, and claims the benefit of U.S. Provisional Application No. 61/362,506, filed Jul. 8, 2010 The entire teachings of the above application are incorporated herein by reference.

BACKGROUND OF THE INVENTION

Stem cell scaffolds, which can be both 2D and 3D in nature, have been fabricated to mimic the intrinsic characteristics of natural substrates such as muscle, bone and cartilage. (Jaiswal, N., et al., *J. Cell Biochem.* 1997, 64, 295; Engler, A. J., et al., *Cell* 2006, 126, 677; Reilly, G. C., et al., *J. Biomech.* 2010, 43, 55). Recently, both the lithographic patterning of suitable surfaces such as polydimethylsiloxane (PDMS), polymethyl methacrylate (PMMA), self-assembled titanium dioxide ($TiO_2$) rod arrays and functionalized carbon nanotubes have been explored. (Kim, S. J., et al. *J. Mater. Sci: Mater. Med.* 2008, 19, 2953; Dalby, M. J., et al., *Nat. Mater.* 2007, 6, 997; Oh, S., et al., *Proc. Natl. Acad. Sci. USA* 2009, 106, 2130; Nayak, T. R., et al., *ACS Nano,* 2010, 4, 7717). While there have been tremendous advances in this field, many challenges still remain. In particular in the field of bone tissue engineering, almost all artificial materials require the administration of multiple growth factors to promote human mesenchymal stem cell (hMSC) differentiation and bioactive implants still suffer from severe limitations including potential pathogenic infections, low availability and high costs. In addition, many modern approaches also face further challenges when it comes to scalability and compatibility with implants.

Therefore, there remains a significant need for development of more biocompatible scaffolds that allow for better scalability of the biocompatible scaffold materials and compatibility with implants.

SUMMARY OF THE INVENTION

In a first main aspect, the invention relates to a method of directing stem cell differentiation in the absence of growth factors or external stimulation, comprising: placing stem cells on a graphene substrate and exposing to a culture media for a period of time sufficient to allow the stem cells to differentiate in cells of interest in the absence of growth factors or external stimulation. The graphene can be single layer, multi-layer, two dimensional or three dimensional. In one embodiment, the culture media is an osteogenic medium.

In one embodiment, the stem cells are mesenchymal stem cells. In another embodiment, the stem cells are progenitor cells.

In another aspect, the invention relates to a method of repairing and improving bone tissue function comprising directing stem cell differentiation by placing the stem cells on graphene, e.g., single layer or multi-layer, in the absence of growth factors or external stimulation and transplanting the graphene with the stem cells in the tissue at the site of repair.

In a further aspect, the invention relates to a composition for accelerating differentiation of human mesenchymal stem cells comprising single layer graphene on an implantable, biocompatible scaffold for support of tissue growth.

In another aspect, the invention relates to the use of graphene as a substrate for stem cell differentiation.

The present invention provides graphene as a low cost, biocompatible scaffold that does not hamper the proliferation of human stem cells and accelerates their specific differentiation into various cell types.

BRIEF DESCRIPTION OF THE DRAWINGS

The foregoing will be apparent from the following more particular description of example embodiments of the invention, as illustrated in the accompanying drawings in which like reference characters refer to the same parts, throughout the different views. The drawings are not necessarily to scale, emphasis instead being placed upon illustrating embodiments of the present invention.

FIG. 1 (*a*) is a graph of cell viability of hMSCs grown on different substrates including silicon wafer with 300 nm $SiO_2$ (Si/$SiO_2$), polyethylene terephthalate (PET), and polydimethylsiloxane (PDMS) in percentage normalized to cover slips used as a reference. FIG. 1 (*b-i*) and inset show cell morphology of hMSCs grown on standard cover slips and on glass slide, Si/$SiO_2$, PET and PDMS with or without graphene. Scale bars are 100 μm.

FIG. 4 (*a*) is an optical image of a 1×1 cm graphene coated Si/$SiO_2$, showing the graphene boundary. FIG. 4 (*b*) shows highly fluorescent osteocalcin (OCN) marker indicating bone cell formation on the same chip only on the graphene coated area.

OCN, marker for bone cells, became visible at Day 4 and very intense by DAY 7. Scale bars are 100 μm.

DETAILED DESCRIPTION OF THE INVENTION

The invention pertains to methods of directing differentiation of stem cells when cultured on graphene, in the presence of osteogenic medium that does not require further supplementation of additional growth factors or replenishment of growth factors. The methods and compositions of the invention may be used for repairing or improving tissue function. The invention is based, in part, upon data reported herein showing that graphene provides a biocompatible scaffold that does not hamper the proliferation of stem cells in stem cell medium and directs the stem cells to specifically differentiate into bone cell types once cultured in osteogenic medium.

Results showed that mono-atomic graphene coated substrates accelerated cell differentiation to a higher extent than un-coated substrates or cover slips. In contrast to other materials, graphene does not require additional chemical inducers (e.g., growth factors including BMP-2) to be continuously added or replenished to the osteogenic medium to achieve cell differentiation. In fact, direct comparison of the effects of graphene and growth factors on stem cell differentiation showed that differentiation rates with graphene were comparable to the ones achieved with common growth factors.

In one aspect, the invention pertains to a method for directing the differentiation of stem cells into cells of interest using graphene as a scaffold for accelerated differentiation. The term "directing differentiation of a stem cell" as used herein is taken to mean causing a stem cell to develop into a specific differentiated cell type. The stem cells are grown on a graphene substrate in an appropriate culture medium under conditions that do not require implementation with growth factors or external stimulation, or combinations thereof. In certain embodiments of the invention, the stem cells or progenitor cells on graphene are grown and differentiated in vitro.

In another aspect, the invention pertains to a method for accelerating stem cell differentiation by culturing stem cells on the graphene substrate. The term "acceleration" as used herein means acceleration of stem cell differentiation on graphene and in the presence of osteogenic media as compared to differentiation only in osteogenic media.

The results reported herein show that graphene provides unique properties that enhance the differentiation of stem cells into cells of interest, particularly bone cells. These differentiated cells on the graphene substrate can be incorporated into bioimplants having improved biocompatibility.

Graphene is a two dimensional sheet of carbon that has highly desirable physical properties for use in tissue regeneration and medical devices. Graphene is the strongest material known having a Young's modulus of 0.5-1 TPa, yet it is extremely flexible and not brittle. Graphene can be transferred onto any flat or irregular shaped surface and graphene-coated, flexible, supporting substrates can be easily bent into any shape required. Being only one atom thick, yet fully continuous it also introduces the minimum amount of non-biodegradable material preventing inflammatory or other immune responses seen with other non-biologic materials. Graphene also serves as an impenetrable gas barrier and can hermetically seal the substrate or implant material, protecting it from any degradation due to external factors. As a result, graphene may significantly strengthen bone structures or eventual implants in addition to serving as a substrate for tissue regeneration and/or repair.

High-quality, continuous graphene sheets can be produced on a large scale through chemical vapor disposition on copper foil. (Bae, S., et al., *Nat. Nano*, 2010, 5, 574). "Chemical vapor deposition (CVD)" refers to a chemical process used to produce high-purity, high-performance solid materials where substrate is exposed to one or more volatile precursors, which react and/or decompose on the substrate surface to produce the desired deposit. For example, graphene can be produced by exposing copper foils to hydrogen and methane at high temperatures which react to form single layer graphene that is deposited on the metal surface. Graphene can be directly deposited onto any substrate, without the need to intercalate any additional material between graphene and substrate. These substrates include, but are not limited to, quartz, polydimethylsiloxane (PDMS), polyethylene terephthalate (PET), and silicon wafer with 300 nm $SiO_2$ ($Si/SiO_2$). In terms of biomedical applications, the substrate of interest could consist of the metal implant or the defective tissue itself.

Substrates that may be used for growing graphene include, but are not limited to, copper (Cu), nickel (Ni), silicon carbide (SIC) and may include also non-metal or non-oxide substrates. Substrates are not limited to planar substrates but can be three dimensional forms of nickel, copper or any other material facilitating the growth of graphene.

Classifications of graphene include, but are not limited to, mechanical exfoliation of graphene, CVD grown graphene, chemically derived graphene oxide, reduced graphene oxide, functionalized graphene, hydrogenated graphene, fluorinated graphene, chemically modified graphene, embedded graphene, silicon carbite based graphene, two-dimensional graphene and three-dimensional graphene. In one embodiment, the graphene is three-dimensional graphene.

"Chemically modified graphene" is graphene whose structure has been chemically altered or modified. Chemical modifications can include, but are not limited to, covalent or ionic linking of agents to the graphene structure or addition or substitution of substituents that may alter the properties of graphene. Examples of agents that may be linked to the graphene include, but are not limited to, growth factors, drugs (e.g., anticoagulants, such as heparin, antibiotics), antibodies, steroids, proteins, amino acids, hormones, peptides or enzymes. Such agents can augment of enhance the healing process or tissue repair.

"Embedded graphene" is intended to embrace any type of graphene where a biochemical agent is incorporated into the graphene during the coating of the substrate or thereafter. Examples of biochemical agents that can be embedded into the graphene are those described above.

The graphene substrate useful in the present invention consists of many micrometer ripples and wrinkles and has a high Young's modulus. The ripples themselves provide local curvature further enhancing the reactivity of the graphene sheets while the high Young's modulus provides the flexibility for the out-of plane deformations which contribute to graphene's cellular differentiation properties. As a result, the ripple and wrinkles lead to the large scale disorder that plays a role in protein adsorption, cell adhesion, proliferation and differentiation.

In one embodiment, graphene is multi-layer graphene. The term "multi-layer graphene" refers to graphene that has multiple layers of single atomic graphene on individual graphene flakes. In one non-limiting embodiment, the graphene has ten to twenty layers. In another embodiment, the graphene has five to ten layers. In yet another embodiment, the graphene has one to five layers. In another embodiment of the invention, the graphene is single layer graphene. As used herein, the term "single layer graphene" refers to a graphene monoatomic sheet that has less than or about 5% two or three layer graphene. For example, graphene grown on copper is self terminating producing single layer graphene that has less than 5% two and three layer graphene flakes. In one non-limiting embodiment, the graphene has about 5% two and three layer graphene. In another embodiment, graphene has less than 5% two and three layer graphene.

According to the invention, a stem cell is cultured in the presence of graphene. In one embodiment, the graphene is in direct contact with the cells. In another embodiment, the graphene is in contact with the culture media, and in direct contact with the cells. For example, stem cells are seeded on graphene coated substrate and then placed in culture media.

A variety of stem cells of various types and stages of differentiation can be used in the invention and include but are not limited to, for example, totipotent, pluripotent, multipotent and unipotent stem cells. In one embodiment of the invention, the stem cell is an embryonic stem (ES) cell. In another embodiment of the invention, the stem cell is a progenitor stem cell. In yet another embodiment, the stem cell is a mesenchymal stem cell.

Of particular interest are mesenchymal stem cells (MSCs) which can differentiate in vitro, in a variety of connective tissues or progenitor cells, including, but not limited to, mesodermal (osteoblasts, chondrocytes, tenocytes, myocytes and adipocytes), ectodermal (neurons, astrocytes) and endodermal (hepatocytes) derived lineages. The term "mesenchymal stem cell" and "marrow stromal cell" are often used interchangeably, so it is important to note that MSCs encompass multipotent cells from sources other than marrow, including but not limited to, muscle, dental pulp, cartilage, synovium, synovial fluid, tendons, hepatic tissues, adipose tissue, umbilical cord, and blood, including cord blood.

While stem cells exemplified herein are differentiated into bone cells, differentiation into any desired "cell of interest" is contemplated. Examples include, but are not limited to, osteocytes, chondrocytes, adipocytes, muscles cells, nerve cells and cardiac myocytes. In one embodiment, the differentiated cell is a chondrocyte. In another embodiment, the differentiated cell is an osteocyte. In another embodiment, the differentiated cell is a cardiac myocytes. In a further embodiment, the differentiated cell is a muscle cell. In yet another embodiment, the differentiated cell is a nerve cell. In another embodiment, the differentiated cell is an osteoblast. In another embodiment, the differentiated cell is an adipocyte. In another embodiment, the differentiated cell is a hepatocyte.

The invention also applies to a variety of stem cells of various types and stages of differentiation, and cultured in media that promotes differentiation toward a particular type of cell. The term "culture media" as used herein means any liquid or solid preparation made specifically for the growth, storage or transport of microorganisms or other types of cells. The variety of media that exist allow for the culturing of specific organisms and cell types, such as differential media, selective media, test media and defined media. In one embodiment, the culture medium is chondrogenic. In another embodiment the culture medium is osteogenic. In another embodiment, the culture medium is myogenic. In another embodiment, the culture medium is neurogenic. In another embodiment, the culture medium is adipogenic. In another embodiment, the culture medium is hepatogenic. For example, human mesenchymal stem cells (hMSCs) can be placed on graphene in osteogenic media to obtain osteogenic differentiation.

Conventional osteogenic medium contains dexamethasone, which can lead to osteogenic differentiation. However, it is usually administered in combination with other agents, growth factors or external stimulants to achieve differentiation through a synergistic effect since differentiation in osteogenic medium occurs over prolonged periods of time. "Growth factors" include naturally occurring substances capable of stimulating cellular growth, proliferation and cellular differentiation. For example, bone morphogenetic protein-2 (BMP-2) is a growth factor that plays an important role in the differentiation of cells into bone and cartilage. As used herein, "external factors" or "external stimulants" are external sources of mechanical, acoustic or electromagnetic energy that can stimulate cellular proliferation and differentiation. For example, radiowaves or electromagnetic radiation can be used to supply cells with the sufficient energy needed to promote cellular growth.

According to the invention, the graphene can be employed not only in tissue culture, but wherever it is desired to stimulate growth and/or repair of bone, cartilage, muscle, or nervous tissue in a host. The stem cells can be cells already present at a particular location, or implanted, or injected. In one embodiment, stem cells are stimulated on graphene in vitro. In a further embodiment, progenitor cells are stimulated directly using graphene. In certain embodiments, the stem cells seeded on graphene are implanted as part of a tissue or prosthesis or treatment of structures so destined for insertion or implantation into a host.

One example of such a structure is a matrix for bone or cartilage growth or regeneration. Examples include, but are not limited to a demineralized bone matrix (e.g., composed primarily of collagen and non-collagenous proteins), devitalized cartilage matrix, or other artificial matrix for bone or cartilage repair. Other porous scaffolds (ceramics, metals, polymers and nano-reinforced) are osteoconductive and promote bone ingrowth, with osteoinductive properties provided by incorporation of peptides, hydroxyapetite and cytokines known to influence bone cells.

In one embodiment, collagen, particularly collagen type II, is used to promote chondrogenic differentiation of stem cells on graphene. In another embodiment, osteogenic matrix is used to promote osteogenic differentiation of stem cells on graphene. In another embodiment, graphene seeded with stem cells is implanted at the regeneration site. In another embodiment, stem cells on graphene are incorporated into an implant or prosthesis. In yet another embodiment, progenitor cells on graphene are incorporated into an implant or prosthesis. In another embodiment, the implant is coated with graphene and osteogenic differentiation is promoted at the implant site. In another embodiment, an implant made of $TiO_2$ or any other medical implant material, is coated with graphene and osteogenic differentiation are promoted at the implant site. In another embodiment, the graphene is grown on the implant and differentiation is promoted at the implant site. In another embodiment, the graphene is a three-dimensional scaffold serving as implant material and differentiation is promoted by the graphene implant. In another embodiment, graphene can be used as bonefilling material. Medical implant materials include, but are not limited to, graphene, metal, metal alloy (e.g., stainless steel or Cobalt Chrome), metal oxide (e.g., $TiO_2$), oxide, ceramic, composite materials and plastics.

Preferably, graphene would be directly implanted at the site of defective tissue, to provide mechanical support while promoting stem cells growth and proliferation in a particular cell lineage. Graphene offers the potential to be further functionalized and/or embedded with biochemical agents to enhance healing process and tissue repair. Also, graphene can be used as a temporary scaffold to direct cell differentiation into a specific lineage, after which, it could be separated from the differentiated cells and completely discharged.

Thus, the matrices can include bone- or cartilage-specific matrix components and are populated with bone or cartilage progenitor cells, which are stimulated according to the invention.

The invention also provides for a composition for stimulating and/or differentiating stem cells or progenitor cells. The compositions are suitable for cell growth and comprise stems cells on a graphene substrate exposed to culture media. In one embodiment, the composition comprises graphene coated or placed on a biocompatible material. In another embodiment, the composition comprises stem cells on a graphene coated biocompatible material. Biocompatible materials can include natural or synthetic materials used to replace part of a living system (e.g., tissue or organ replacement) or to function in intimate contact with living tissue.

The method of the invention is also applied to the manufacture and use of medical implants, such as an orthopedic or a dental implant. The implant can be a metal implant, such as an artificial hip, knee, or shoulder, to which the bone must meld. Other examples include dental implants. The implants are prepared with graphene attached surfaces that are to be fused to bone, providing an improved surface that enhances growth of bone forming cells. The implant can also be made of a composite material such as a fiber composite. For example, orthopedic implants can be made from composite material strengthened by the addition of graphene. The implants can be implanted directly, or incubated with osteoblasts from the recipient prior to implantation.

When implanted or injected, stem cell development is often governed by the site of implantation or the site in the body to which the stem cell is home. According to the invention, differentiation of stem cells and progenitor cells can also be directed in vitro by selection of media components and/or matrix components. For example, cytokines, and growth factors that promote osteogenic differentiation include various isoforms of bone morphogenetic protein (BMP) such as BMP-2, -6, and -9, interleukin-6 (IL-6), growth hormone and others. (See, e.g., Heng et al., 2004, J. Bone Min. Res. 19, 1379-94). Cytokines and growth factors that promote chondrogenesis include various isoforms of TGF-β and bone morphogenetic protein, activin, FGF and other members of the TGF-β superfamily. Osteogenesis of chondrogenesis is favored by naturally occurring or synthetic cartilage extracellular matrix (ECM) material. For example chondrogenesis is favored by naturally occurring or synthetic ECM. Such an ECM can comprise collagenous proteins such as collagen type II, proteoglycans such as aggrecan, other proteins and hyaluronin. (See, e.g., Heng et al., 2004, Stem Cells 22, 1152-67). Phenotypic markers expressed by cells of the various lineage are well known in the art.

The invention further provides kits for differentiating stem cells. The kits comprise graphene for controlled and accelerated differentiation of the stem cells. The graphene can be provided separately from the stem cells or coated on the containers used for culturing stems cells. In another embodiment, the kit contains graphene incorporated onto a support, such as a scaffold on or within which stem cells or progenitor cells are stimulated and/or differentiated. In a further embodiment, the kits contain instructions on how to use the invention to obtain stimulated or differentiated cells using graphene and the appropriate culture media. Optionally, the kits further contain media formulations selected to promote differentiation to osteocytes, chondrocytes, or other differentiated cell types. Suitable media include, but are not limited to, adipogenic media, osteogenic media, chondrogenic media, myogenic media, neurogenic media, hepatogenic media In one embodiment of the invention, the differentiated stem cells are used to identify and/or isolate biological compounds, including but not limited to proteins and nucleic acids characteristic of the stimulated or differentiated state of the cells. Such biological compounds are useful for example, as markers of differentiation and as targets for antibodies and other agents. Fluorescent antibodies, specific for immunostaining of typical proteins produced by defined cell lines, can be used to confirm whether differentiation has occurred or not. A few examples are the fluorescent antibody for CD-44 (which is typical of MSCs), or DESMIN (D-33, specific for muscle cells), or antibody for MAP-2 (used as a marker for neurons) or OCN (specific for osteocytes) or $\beta_1$-integrin (protein produced when cells have increased adhesion to the substrate underneath). As an example, hMSCs incubated in osteogenic media for 14 days, show the ability to bind OCN only in the presence of graphene-coated substrates, while they immunostain for CD-44 on cover slips or uncoated substrates.

Experimental Procedures

Substrate Preparation

Graphene was grown on copper foils by chemical vapor deposition at 1000° C. in a mixture of hydrogen and methane as discussed elsewhere. (Li, X., et al., *Science* 2009, 324, 1312). The graphene film was mechanically supported by a thin film of polymethyl methacrylate (PMMA) (Microchem) and the copper foil was etched in a weak solution of ammonium persulfate (Sigma). The graphene coated with PMMA was transferred to deionized water to remove residues and the transfer was completed by gently contacting graphene with the substrate and lifting it out of the water. To avoid any residues from the transfer process the samples were left in warm acetone for 12 hours followed by 3 hours in isopropanol. In a final step the $Si/SiO_2$ substrates were annealed in $Ar/H_2$ 90/10 wt % for 7 hours at 300° C. to further reduce impurities in the graphene layer. However, note that $Si/SiO_2$ without the additional step of annealing showed the same cell viability and induced stem cell differentiation at the same rate (data not shown).

Large-scale graphene used in this study was synthesized by the chemical vapor deposition method on copper foils. After growth, copper was etched and the same batch of graphene was transferred to four distinct substrates used in this study according to methods discussed elsewhere. (Li, X., et al., *Science* 2009, 324, 1312) The influence of graphene on stem cell growth was studied by investigating four distinct substrates with widely varying stiffness and surface roughness: (1) polydimethylsiloxane (PDMS), (2) polyethylene terephthalate (PET), (3) glass slide and (4) silicon wafer with 300 nm $SiO_2$ ($Si/SiO_2$). Plain cover slips without graphene were used as a control or reference for normalization. Atomic Force Microscopy (AFM) was used to analyze the surface roughness of the various substrates with and without graphene coating.

Transferred to PET, PDMS, and Si/SiO$_2$, the graphene sheet exhibits nano-ripples with high density compared to graphene on glass slide. Despite being only one atom thick, on Si/SiO$_2$ substrates with well-defined oxide thickness, graphene can be easily seen with a simple conventional optical microscope. First cell viability was studied with cells cultured in normal stem cell medium. Next, stem cell differentiation was examined in cells cultured on conventional osteogenic media.

Cell Lines and Markers

Human mesenchymal stem cells (hMSCs) were purchased from ATCC and cultured in low-glucose Dulbecco's modified eagle medium (Sigma) supplemented with 10% FBS (Invitrogen), 1% penicillin/streptomycin (Gibco), 1% Non-essential amino acids (Sigma) and 1% sodium pyruvate (Sigma). hMSCs at passage 2 were used in this study. Osteogenic medium consisting of DMEM basal medium (Sigma) added with dexamethasone, L glutamine, ascorbic acid and Beta-glycerophosphate was prepared according to a known procedure. (Fahmi, H., et al., *Osteoarthritis and Cartilage* 2002, 10, 845). FITC-Goat anti mouse antibody was purchased from Biolegend, San Diego, Calif. (USA). Markers (osteocalcin (OCN), CD44, Desmin (D33), MAP-2, $\beta_1$-integrin) were purchased from Acris Antibodies GmbH (Germany).

Cell Viability and Morphology Mesenchymal Cells in the Presence of Graphene.

hMSCs Differentiation into Osteogenic Lineage.

hMSCs (20,000 cells/well (24 well plate)) were seeded on uncoated (control) and graphene coated (test) chips and cultured in normal stem cell medium. Post confluence (2 weeks), cells growing on each chip were transferred to new well plate and washed 3 times with 2 ml of PBS. 1 ml of PBS was added to each well followed by 5 µl of 1 mM Calcein acetoxymethyl ester (Calcein AM) and incubated at room temperature for 15 minutes. After removing the unbound stains, the chips were inverted on to glass slides mounted with vectashield with 4,6'diamidino-2-phenylindole (DAPI) (H 1200, Vector labs) and visualized under fluorescence microscope (Nikon AZ-100 multipurpose microscope). Pictures were taken at 4 different positions of the chips and processed by image J software to count the number of viable cells to the number of nucleus as determined by staining with DAPI. Cell viability was measured by comparing the cell numbers for each substrate with the cells counted on cover slips. In addition, (3-(4,5-Dimethylthiazol-2-yl)-2,5-diphenyltetrazolium bromide (MTT) assays were carried out, in which cytotoxicity evaluation was based on the activity of enzymes to reduce MTT to formazan dyes, giving a purple colour. (Mosmann, T., *J. Immun. Met.* 1983, 65, 55). Experiments were carried out in triplicates, following the procedure reported in supporting document. The morphology of the hMSCs on different substrates was compared according to the image as seen in the form of calcein AM staining (FIG. 1).

Cell cytotoxicity of graphene was tested by comparing cell counts for all four substrates with and without graphene coverage and found that graphene does not hamper stem cells' normal growth over the whole period of investigation (1-18 days). On the contrary, MTT assay showed that cells grew better on graphene covered substrates in particular on the softest substrates, i.e. PDMS and PET. From FIG. 1 (*a*) it can be seen that, independent of the substrate, there is no significant difference (p>0.05) in cell viability between graphene-coated and uncoated substrates. MTT assays were also performed to confirm the cell viability data. Again, regardless of the substrate, there was no difference (p>0.05) between uncoated and graphene-coated substrates, demonstrating that cell growth was indeed not affected by the presence of graphene. Note that cell viability is lower on PET and PDMS independent of the presence of graphene.

Figure 1:
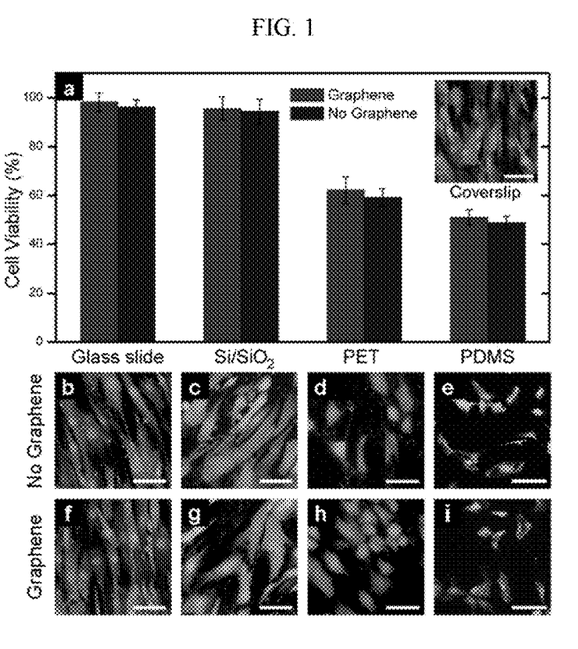

A similar conclusion can be reached by just comparing cell morphology with and without graphene (FIG. 1 (*b-i*)). In general, the presence of graphene did not influence the shape of the cells in comparison to uncoated substrates. Mesenchymal stem cells maintained their spindle-shape across glass slides and Si/SiO$_2$ after 15 days of incubation. Here stem cells presented the usual elongated structure with noticeable filopodia extensions and cellular propagation fronts. In the case of PET and PDMS, cells showed rounded or irregular morphology, most probably due to poor adhesion to the substrate. This suggests that graphene does not hamper the normal growth of stem cells and that the incorporation of this material in implants or injured tissues would not affect the physiological conditions of the microenvironment. In fact, Raman measurements and visual inspection of the samples after cell incubation and subsequent removal clearly showed that the graphene sheets remained largely intact.

Figure 2:
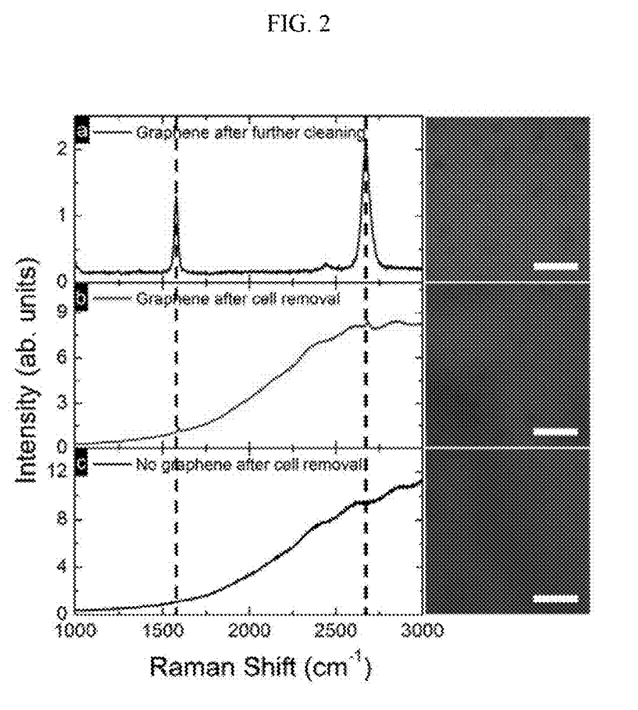
FIG. 2 shows Raman analyses and optical images of (a) graphene on Si/$SiO_2$ after removal of cells and cleaning with acetone, (b) graphene on Si/$SiO_2$ after removal of cells and (c) Si/$SiO_2$ after removal of cells. Scale bars are 10 μm.

Raman spectra of graphene on Si/SiO$_2$ after cell removal and subtraction of the background, clearly show the G and 2D peaks, which represent the Raman "fingerprints of graphene" (FIG. 2). Note also, that the absence of the D-peak at 1350 cm$^{-1}$ indicates the lack of defects to the graphene crystal lattice (Ferrari et al. *PRL*, 2006, 97, 187401). The optical images also clearly shows that the graphene sheet remains largely intact.

Immunofluorescence of hMSCs hMSCs at 20,000 cells/well (24 well plate) were seeded, osteoinduced and incubated up to confluence (2 weeks) as reported above. The cells on all the chips were fixed by treating them with ice cold 50%/50% methanol/acetone. After 5 minutes, methanol/acetone was removed and the chips were left open inside the laminar hood to be air dried. After the chips were completely dried, the fixed cells were treated with 10% FBS (blocking agent) in PBS for 20 minutes. The blocking agent was aspirated out and 5 µl of different antibodies to cellular markers (CD-44 for hMSCs, OCN for osteoblasts, Desmin for muscle cells and MAP2 for neuronal cells) were added on to separate chips (previously marked). After 1 hour the cells on the chips were extensively washed in Millie water for 5 minutes and then rinsed in PBS 1× for 5 minutes. After that, 100 µl of diluted (1/100) FITC-goat antimouse antibody were added on to each chip and incubated at room temperature. After 30 minutes the cells were washed with MilliQ™ water for 5 minutes and then rinsed in PBS 1× for 5 minutes. The chips were inverted on to glass slides mounted with vectashield with DAPI (H 1200, Vector labs) and visualized under fluorescence microscope (Nikon AZ-100 multipurpose microscope).

Osteogenic differentiation was evaluated over a time frame of two weeks. Uncoated substrates were subjected to BMP-2 (75 ng/mL, added every 3 days) and compared to graphene coated substrates at 1 hour and at Day 1, 4, 7, 10 and 15 in terms of binding to CD-44 (which stains hMSCs), $\beta_1$-integrin (which indicates cell-substrate adhesion) and OCN (which indicates bone cells). The above mentioned procedure was followed for the immunofluorescence and imaging purposes.

Figure 3:
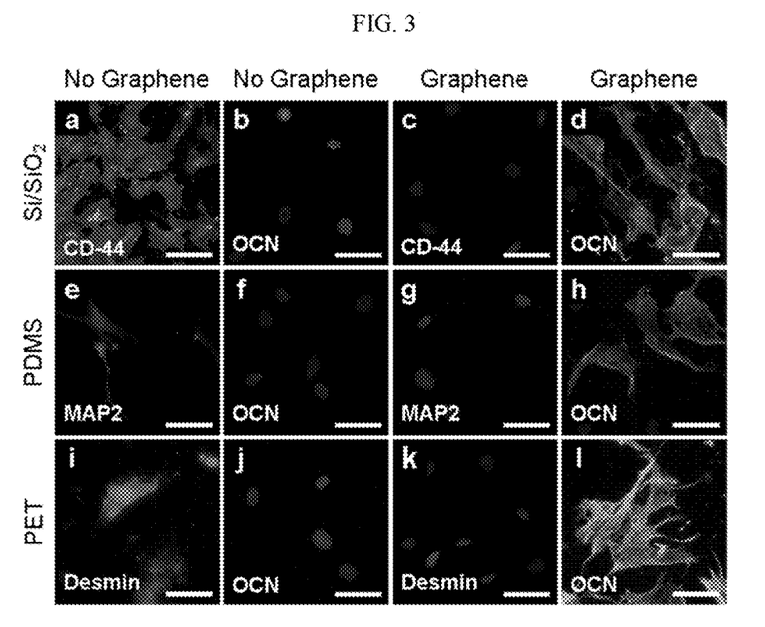
FIG. 3 shows immunostaining of cells growing on Si/$SiO_2$, PDMS and PET without BMP-2 growth factor. Cells are stained with DAPI (blue) and either CD-44, MAP2, Desmin or Osteocalcin (OCN) as indicated (green). (a-d) Cells growing on Si/$SiO_2$, without graphene showing presence of CD-44, and with graphene showing presence of OCN. (e-h) Cells growing on PDMS without graphene showing some MAP2 immunostaining, and with graphene showing staining of OCN. (i-1) Cells growing on PET without graphene showing some staining of desmin, and with graphene showing OCN immunostaining. Scale bars are 100 μm.

Next, specific markers were used to determine the conversion of hMSCs into specific cell types when cultured in osteogenic media. Note that conventional osteogenic medium does contain dexamethasone, which can lead to osteogenic differentiation by itself. However, it is usually administered in combination with other agents and growth factors such as BMP-2 to achieve differentiation through a synergistic effect. In none of the un-coated substrates studied here, the osteogenic medium alone was sufficient to lead to osteogenic differentiation over the whole duration of the experiment (15 days). In the absence of graphene, stem cells on cover slips, on glass slides and on $Si/SiO_2$ did not differentiate: this was demonstrated by immunofluorescent staining of two typical protein markers, namely CD-44 for hMSCs and osteocalcin (OCN) for osteoblasts (FIG. 3). These three substrates showed a CD-44-positive staining and the absence of OCN. However, once these stiff substrates were coated with graphene, hMSCs lost their ability to bind the fluorescent antibody specific for CD-44 expression, suggesting they underwent a different fate. In fact, hMSCs immunostained for OCN, indicating osteogenic differentiation. On uncoated PDMS, hMSCs did not stain CD-44 but they showed a weak expression of MAP2 (typical neuronal marker). On the other hand, in the case of uncoated PET, desmin (D33, a muscle cell marker) staining but not CD-44 was observed. However, once coated with graphene, hMSCs growing also on these softer substrates bound specifically to OCN only, demonstrating that graphene is the driving force of bone cell formation, regardless of the underlying substrate.

Figure 4:
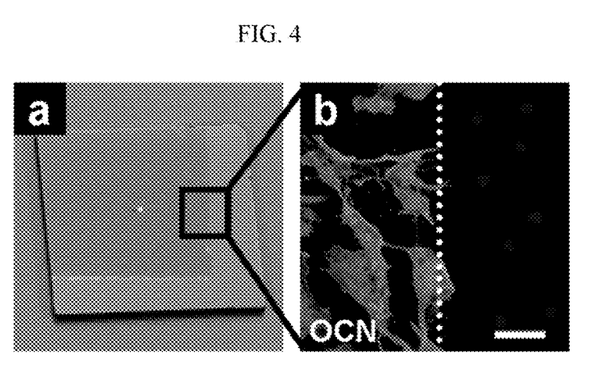

This is most clearly seen in the immunofluorescent staining of cells on a $Si/SiO_2$ wafer, which are cultured in osteogenic medium but only partially covered by graphene. Despite the stiffness of the substrate, specific immunostaining for OCN was only observed in the area covered by graphene. The boundary separating the graphene coated region from the uncoated region is clearly visible even from the immunofluorescent image (FIG. 4).

Alizarin Red Staining and Quantification hMSCs (20,000 cells/well (24 well plate)) were seeded in to the control and the test well plate. After 24 hours, osteogenesis was induced by replacing the original medium with osteogenic medium, which was changed every 3 days up to confluence (2 weeks).

Alizarin red staining was performed using the protocol adapted from Chemicon Mesenchymal Stem cell Osteogeneis kit Cat. No. SCR028. Briefly, the medium was aspirated out from each well and cells were fixed with ice cold 70% ethanol for 1 hour at room temperature. Then the cells were rinsed twice with MilliQ™ water followed by addition of 2 ml of alizarin red (Sigma) solution for each well and incubated for 30 minutes. Finally the unstained alizarin red was washed with MilliQ™ water and the chips were visualized under microscope (Nikon eclipse TE2000-U, Japan). Cells with calcium deposits due to bone nodule formation were stained red. Alizarin red quantification was done using a previously reported procedure. (Tataria, M., et al., *J. Pediatr. Surg.* 2006, 41, 624).

Alizarin Red assay is used to assess the presence or absence of calcium deposits due to bone nodule formation.

Figure 5:
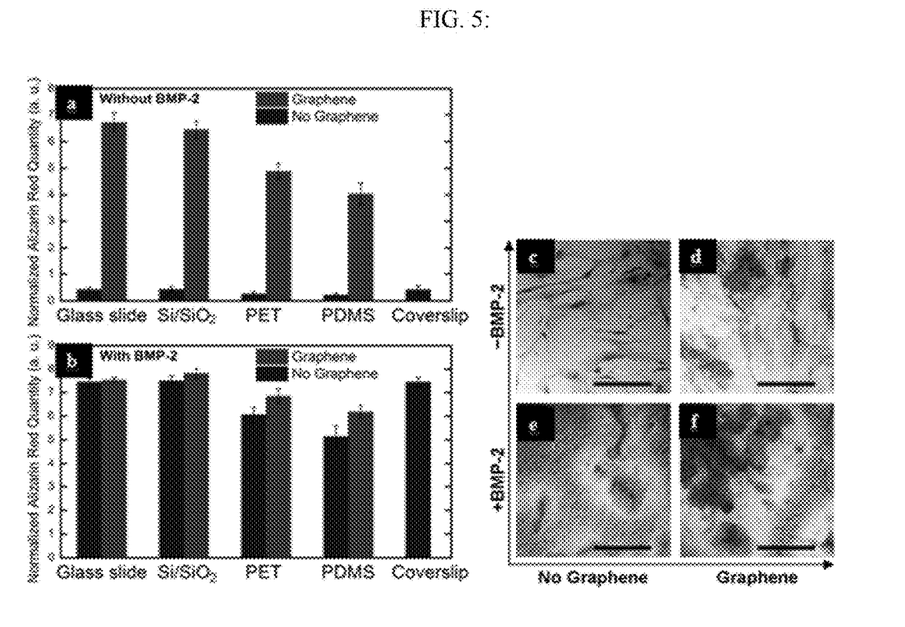
FIG. 5 shows a quantitative, functional proof of graphene-mediated hMSCs' differentiation into osteocytes via Alizarin Red assay, (i) in the presence (dark gray bars) or absence (black bars) of graphene, (ii) in the absence (a) or presence (b) of additional growth factor BMP-2. Conventional plain cover slips were used as a positive control. (c-f) Qualitative staining via alizarin red assay of calcium deposits on PET substrates due to osteogenesis. (c) PET without BMP-2 and without graphene; (d) PET without BMP-2 and with graphene; (e) PET with BMP-2 and without graphene; (f) PET with both BMP-2 and graphene. Scale bars are 100 μm.

The extent of calcium deposition on each substrate was compared using the alizarin red staining results, with and without graphene coating, in the absence of the typical growth factor BMP-2 (FIG. 5). A strong increase in calcium deposit with graphene coating is observed for all substrates. While the effect is more pronounced with the stiffer substrates, surprisingly graphene had a similar effect also on the softer substrates PET and PDMS. It should be noted that in the absence of growth factors both PDMS and PET are known to be less favorable towards osteoblasts. (Konttinen, Y. T., et al., *Clin. Orthop. Relat. Res.* 2005, 430, 28). Yet the presence of graphene induced a drastic change of their natural behavior similar to what has been observed with apatite coating on such polymers. (Kawai, T., et al., *Biomat.* 2004, 25, 4529; Kim, H.-M., et al., *J. Mat. Sci. Mater. Med.* 2000, 11, 421; Kim, H.-M., et al., *J. Biomed. Mater. Res.* 1999, 46, 228). Osteogenic medium alone was not sufficient to induce differentiation: within the 15 day time frame of the experiment, the control represented by cover slips in osteogenic medium without graphene, i.e. hMSC cultured on ordinary tissue culture plate, did not show any calcium deposition.

The impact of graphene on softer substrates such as PET became even more evident in a parallel study, where graphene's influence to that of BMP-2 was directly compared after 15 days of incubation (FIG. 5). In the absence of both graphene and BMP-2, no bone nodule formation was observed as indicated by negative alizarin red staining. As expected, positive staining with identical samples after the addition of BMP-2 was observed. On the other hand graphene-coated PET showed a positive staining even without BMP-2. Experiments were also performed where both graphene coating and BMP-2 treatment were combined. In the case of PET and PDMS, significant enhancement of calcium deposits were observed compared to the above-mentioned samples, which were either only coated with graphene or only treated with BMP-2. This enhancement was specific to soft substrates, and much less evident on the stiffer glass slides and $Si/SiO_2$.

FACS Analysis (Flow Cytometry Experiments)

The hMSCs grown on different substrates (i.e. cover slips, uncoated-$Si/SiO_2$ and graphene-coated $Si/SiO_2$) were subjected to differentiation with osteogenic medium (in the presence or absence of BMP-2) and analyzed after 14 days by fluorescent-activated cell sorting (FACS). The harvested cells were fixed with 4% paraformaldehyde by incubating for 20 minutes. After centrifugation at 1500 RPM for 5 minutes and washing with PBS, the cell pellets were suspended in 100 mM glycine for 10 minutes to quench. The cells were then again centrifuged and washed with PBS and permeabilized by incubating in 50 µl of 0.1% Triton X for 30 minutes. Subsequently, the cells were washed with PBS and were incubated with mouse antihuman osteocalcin antibody for 30 minutes at room temperature. The cells were further washed with PBS and incubated with FITC conjugated goat anti mouse IgG for another 30 minutes. Finally the cells were washed 2-3 times with PBS and were analyzed using BD LSR II flow cytometer (Becton Dickinson).

FACS histogram confirmed negligible osteocalcin positive cells in case of hMSCs on substrates incubated in normal medium. The expression of osteocalcin was maximal for all the substrates in osteogenic media with both graphene and BMP-2. This is similar to the results obtained with the alizarin red quantification and confirms the synergistic effect when both graphene and BMP-2 were concurrently present. Interestingly, osteogenic medium with graphene, but in the absence of BMP-2, reached almost the same levels of cell differentiation (83%) as those in osteogenic medium with both graphene and BMP-2 (100%).

Time Dependence of Differentiation.

Figure 6:
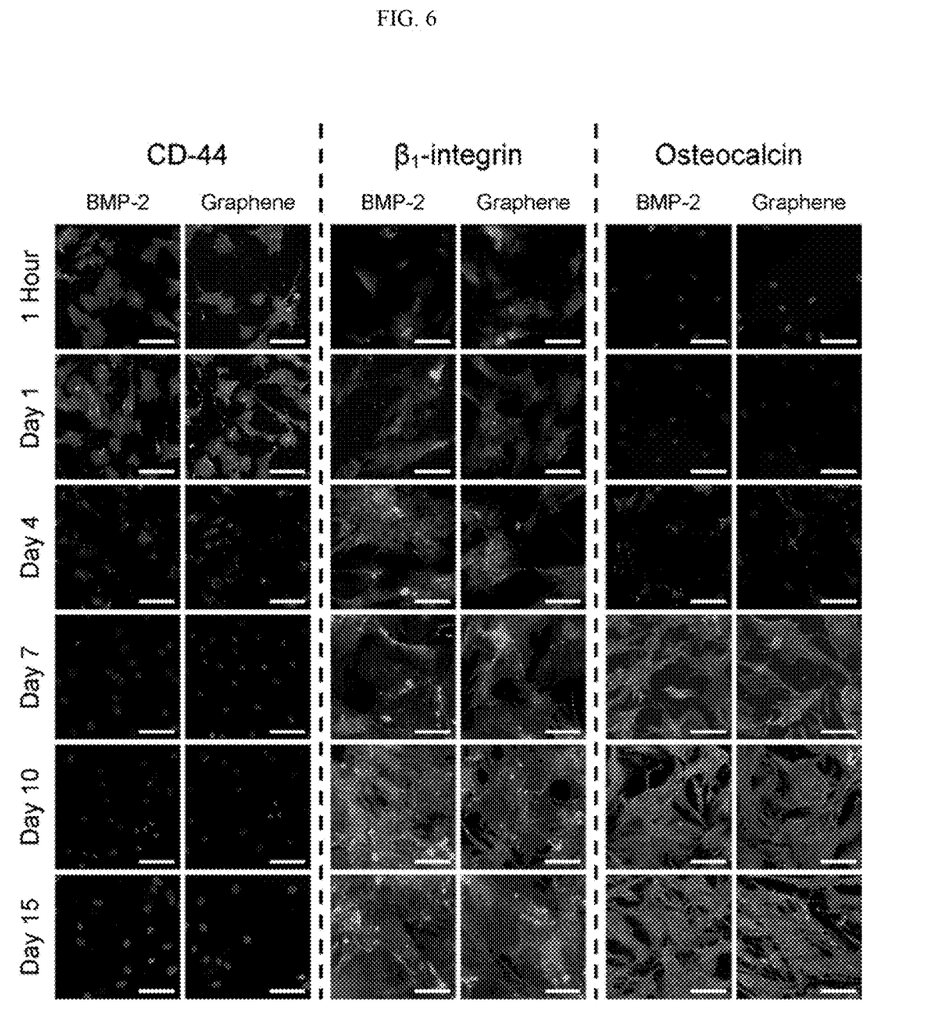
FIG. 6 shows time-dependent immunostaining of hMSCs growing on Si/$SiO_2$ substrates either treated with BMP-2 or coated with graphene. Experiments were performed from 1 hour to 15 days. (Left) CD-44, marker for stem cells, decreased over time and completely disappeared by Day 7. (Center) β1-integrin, marker for cell-substrate adhesion, increased over time, reaching its peak by Day 15. (Right)

An important parameter for practical applications is also the time a material takes to induce bone cell differentiation. To that purpose a study was conducted to see how fast cells on graphene-coated $Si/SiO_2$ substrates differentiate over a time frame of 15 days in comparison to cells growing on uncoated $Si/SiO_2$, but treated with BMP-2 (FIG. 6). These samples were studied at specific time points of 1 hour and 4, 7, 10 and 15 days. Interestingly, both BMP-2-treated and graphene coated substrates were able to induce cell differentiation at the same rate. More precisely, hMSCs on neither substrate showed any sign of osteoblast formation until Day 4. This is demonstrated by the intensity of fluorescence due to CD-44 marker, which is characteristic for stem cells and clearly visible already after one hour of incubation. Conversely, fluorescence due to CD-44 decreased remarkably by DAY 4 and completely disappeared by DAY 7. On the other hand, a progressive enhancement of fluorescence was observed due to OCN (indication of terminal osteogenic differentiation) and $\beta_1$-integrin, a protein indicating cell-substrate interaction. The results confirmed a successful differentiation into bone cells with a strong adhesion to the substrates by DAY 7 for both types of samples. $Si/SiO_2$ substrates treated with a) only BMP-2 and b) only graphene were able to accelerate cell differentiation at the same rate over a period of 15 days of incubation. Equally important, in contrast to graphene, BMP-2 needed to be administered every three days during the course of the experiment due to the very short half-lives of BMP-2 again showing graphene as a worthy replacement of biochemical growth factors. (Balmayor, E. R., et al., *Clin. Orthop. Relat. Res.* 2009, 467, 3138; Dragoo, J. L., et al., *J. Orthop. Res.* 2003, 21, 622). Control Experiments.

To confirm that graphene is critical for the observed stem cell differentiation, control experiments were performed with both amorphous carbon thin films and highly oriented pyrolytic graphite (HOPG) samples. Following identical experimental protocols, it was observed that while both types of samples did support cell proliferation, none of them led to cell differentiation.

Cells were cultured on graphene or HOPG in osteogenic medium. After 4 days the fluorescence deriving from the antibody specific for CD-44 expression was significantly lower for cells grown on graphene than for cells on HOPG. At the same time, specific immunostaining for OCN was already detectable with cells grown on graphene, while only the DAPI stained nuclei were visible for cells on HOPG.

The observed effect is almost certainly due to a complex interplay of mechanical, chemical and electrical properties of graphene and the interactions between graphene and cells, as well as graphene and supporting substrates. The disparities between the results obtained with graphene and HOPG point towards mechanical properties and surface morphology as the decisive factors. AFM images of graphene and HOPG clearly show the difference in their topography. While locally (~1001 nm) the two systems have comparable surface morphology, on a larger scale they look very different. CVD graphene consists of many ripples and wrinkles on the micron scale. Such localized out-of plane deformations are completely absent in HOPG graphite, the surface of which consists instead of a large number of micron size terraces.

The fact that (HOPG) graphite is made out of weakly bound graphene planes may be equally important. In the presence of lateral forces such materials easily shear off and are therefore, commonly used in lubricants. In the specific context of cell adhesion and in view of the (lateral) contractual forces cells exert on the surface, this effect may hamper strong cell adhesion. Note that cells can mechanically "sense" lower lying layers down to several tens of micrometers. In the case of graphene, the cells sense the underlying (amorphous) substrate instead.

CONCLUSIONS

To summarize, the presence of graphene did not influence the shape and the growth of the cells in normal stem cell media, demonstrating biocompatibility and suggesting that the incorporation of this material in implants or injured tissues would not affect the physiological conditions of the microenvironment. In the presence of an osteogenic medium, graphene-coating helped by remarkably accelerating the differentiation of hMSCs at a rate comparable to differentiation under the influence of BMP-2. This represents a critical aspect to its successful use for stem cell-based regenerative medicine strategies. In contrast to other substrates, graphene is neither brittle nor does require further nanoscale patterning or functionalization. In addition it is scalable and provides a cost effective way to prepare scaffolds for biological tissues. Currently graphene is only available in form of sheets and we envision a promising role of graphene located between implants and the surrounding tissues. However, the conditions under which graphene is grown are being constantly improved. There is for example a strong effort in establishing graphene growth at much lower temperatures. Thus, growth on alternative biocompatible and biodegradable surfaces, potentially even without the need to resort to catalytic metal films, seems feasible. Even the growth on 3D scaffolds has recently been demonstrated. (Chen, Z., et al., *Nat. Mater.*, 2011, doi:10.1038/nmat3001).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of directing stem cell differentiation in the absence of growth factors and an external stimulant that can stimulate cellular proliferation and differentiation, comprising:
   placing stem cells on a continuous single-layer 2D graphene sheet coated on a substrate and exposing to a culture medium for a period of time sufficient to allow the stem cells to differentiate, in the absence of growth factors and an external stimulant that can stimulate cellular proliferation and differentiation, to produce differentiated cells.

2. The method of claim 1, wherein the stem cells are mesenchymal stem cells.

3. The method of claim 1, wherein the stem cells are progenitor cells.

4. The method of claim 1, wherein the graphene sheet is in the culture medium.

5. The method of claim 1, wherein the culture medium is a stem cell medium.

6. The method of claim 1, wherein the culture medium is an osteogenic medium.

7. The method of claim 1, wherein the stem cell differentiation is osteogenic differentiation.

8. The method of claim 1, wherein the differentiated cells are osteoblasts or osteocytes.

9. The method of claim 1, wherein the substrate is a biocompatible material.

10. A method of repairing and improving bone tissue function comprising directing stem cell differentiation by placing stem cells on a continuous single-layer 2D graphene sheet coated on a substrate; exposing the stem cells to a culture medium for a period of time sufficient to allow the stem cells to differentiate, in the absence of growth factors and an external stimulant that can stimulate cellular proliferation, to produce differentiated stem cells; and transplanting the differentiated stem cells in the tissue at site of repair.

11. The method of claim 10, where the stem cells are mesenchymal stem cells.

12. The method of claim 10, where the culture medium is osteogenic medium.

13. A method of directing stem cell differentiation into osteogenic cells, comprising:
    placing stem cells on a continuous single-layer 2D graphene sheet, produced by chemical vapor deposition, coated on a substrate and exposing to an osteogenic culture medium that is not supplemented with Bone Morphogenetic Protein-2, for a period of time sufficient to allow the stem cells to differentiate into osteogenic cells.

14. The method of claim 13, wherein the osteogenic cells are osteoblasts.

\* \* \* \* \*

UNITED STATES PATENT AND TRADEMARK OFFICE
CERTIFICATE OF CORRECTION

PATENT NO. : 10,316,290 B2
APPLICATION NO. : 13/805328
DATED : June 11, 2019
INVENTOR(S) : Barbaros Oezyilmaz et al.

Page 1 of 1

It is certified that error appears in the above-identified patent and that said Letters Patent is hereby corrected as shown below:

In the Claims

In Claim 10, starting at Column 14, Line 67 and ending at Column 15, Line 1, delete "cellular proliferation," and insert -- cellular proliferation and differentiation, --.

Signed and Sealed this
Twenty-seventh Day of August, 2019

Andrei Iancu
*Director of the United States Patent and Trademark Office*